(12) United States Patent
Sasano et al.

(10) Patent No.: US 6,203,597 B1
(45) Date of Patent: Mar. 20, 2001

(54) METHOD AND APPARATUS FOR MASS INJECTION OF SAMPLE

(75) Inventors: Ryoichi Sasano; Kazuhiko Yamazaki; Masahiro Furuno, all of Iruma (JP)

(73) Assignee: G. L. Scince, Inc. (JP)

( * ) Notice: Subject to any disclaimer, the term of this patent is extended or adjusted under 35 U.S.C. 154(b) by 0 days.

(21) Appl. No.: 09/291,461

(22) Filed: Apr. 14, 1999

(30) Foreign Application Priority Data

Apr. 15, 1998 (JP) .................................................. 10-121727

(51) Int. Cl.[7] .................................................. B01D 15/08
(52) U.S. Cl. .................................... 95/87; 95/89; 96/105
(58) Field of Search .................................. 95/82, 86, 87, 95/89; 96/101, 105

(56) References Cited

U.S. PATENT DOCUMENTS

| | | | |
|---|---|---|---|
| 4,035,168 | * 7/1977 | Jennings | 95/87 X |
| 4,422,860 | * 12/1983 | Feinstein | 95/87 |
| 4,559,063 | * 12/1985 | Munari et al. | 95/89 X |
| 4,734,107 | * 3/1988 | Trestiamu et al. | 95/89 X |
| 5,252,109 | * 10/1993 | Munari et al. | 95/89 X |
| 5,545,252 | * 8/1996 | Hinshaw et al. | 95/82 X |
| 5,714,677 | * 2/1998 | Parsy et al. | 95/89 X |
| 5,944,877 | * 8/1999 | O'Neil | 95/87 X |

OTHER PUBLICATIONS

Large Volume Injection in Capillary GC Using PTV Injectors: Comparison of Inertness of Packing Materials, vol. 18, Journal of High Reoslution Chromatography & Chromatgraphy Communications, pp. 124–128, published Feb. 1995.

"Characterization of Polymers by Multi–Step Thermal Desorption/Programmed Pyrolysis Gas Chromatography Using a High Temperature PTV Injector", vol. 19, Journal of High Resolution Chromatography & Chromatography Communications, pp. 193–199, Apr. 1996.

"Co–Solvent Effects for Preventing Broadening Loss of Early Eluted Peaks when Using Concurrent Solvent Evaporation in Capillary GC", vol. 11, Journal of High Resolution Chromatography & Chromatography Communications, pp. 388–394, May 1988.

* cited by examiner

Primary Examiner—Robert H. Spitzer
(74) Attorney, Agent, or Firm—Oldham & Oldham Co., L.P.A.

(57) ABSTRACT

To enable the mass injection of a sample in a gas chromatography and prevent occurrence of residue or decomposition of a desired constituent during analysis. The invention calls for providing the injection port with a liner, connecting the column and the liner to a press-fit, evaporating the solvent introduced into the liner, and discharging the evaporated solvent from a discharge port formed at the upper part of the liner.

11 Claims, 16 Drawing Sheets

METHOD AND APPARATUS FOR MASS INJECTION OF SAMPLE

FIELD OF THE INVENTION

The present invention relates to a method and an apparatus for mass injection of a sample.

BACKGROUND OF THE INVENTION

One of typical methods of injecting a large quantity of sample during gas chromatography is a PTV (programmed temperature vaporizer) method with or without a split for discharging the solvent. This method calls for a liner disposed at the injection port, and filling the liner with a filler in order to introduce as much sample as possible into the injection port. When in use, the temperature in the injection port has to be maintained so as not to exceed the boiling point of the solvent for the sample. Said method then calls for injecting a great quantity of sample into the injection port so that the sample is retained in the filler; introducing a great quantity of carrier gas in the state where the temperature is still maintained low so that most of the solvent is discharged through a vent line and that the system becomes a splitless state; and introducing the desired constituent that is trapped in the filler in the liner into a column while increasing the temperature in the injection port. Other than the PTV method, various methods on which research and investigations have conventionally been conducted include the on-column mass injection method, which calls for increasing the temperature of the oven and causing pressure equilibrium of the sample in the column in order to remove only the solvent.

A method which calls for filling a split liner with glass wool, a collector or the like to discharge the solvent presents the possibility of the desired constituent remaining in the filler or being decomposed during the thermal desorption process. It is a common knowledge that decomposition actually occurs with some agricultural chemicals. On the other hand, the on-column mass injection method presents a problem in that it takes a long period of time to remove the solvent. Furthermore, as it is difficult to fulfill the conditions for attaining equilibrium in the column, the desired constituent tends to spread into a wide area, thereby necessitating re-condensation.

SUMMARY OF THE INVENTION

In order to solve the above problems, an object of the present invention is to provide a sample injection method and an apparatus for mass injection of a sample, wherein the time required by elimination of a solvent can be reduced by using a splitless liner which is capable of split-purging and by discharging the solvent through the opening of a split purge; no filler is used so that occurrence of residue or decomposition of the desired constituent is prevented; the manner of concentration is at-column concentration conducted at a point in the column so that there is no need of a separate process of re-concentration; there is virtually no influence of the injection rate; and mass injection of a sample is possible. The first feature of the invention lies in providing the injection port with a liner, connecting the column and the liner to a press-fit, evaporating the solvent introduced into the liner, and discharging the evaporated solvent from a discharge port formed at the upper part of the liner. The second feature of the invention lies in providing the injection port with a liner, connecting the column and the liner to a press-fit, introducing a solvent and a sample into the liner and controlling the respective temperatures in the injection port and the oven so as to discharge the evaporated solvent from a discharge port formed at the upper part of the liner while accumulating and concentrating the desired constituent in the sample at the entrance of the column. The third feature of the invention lies in limiting the temperature in the injection port to no higher than the boiling point of the solvent and the temperature of the oven to no lower than the boiling point of the solvent. The fourth feature of the invention lies in providing the injection port with a liner, connecting the column and the liner to a press-fit, providing the body of the injection port with a split, and forming a discharge port for discharging vapor of evaporated solvent at the upper part of the liner.

DETAILED DESCRIPTION OF THE INVENTION

Figure 1:
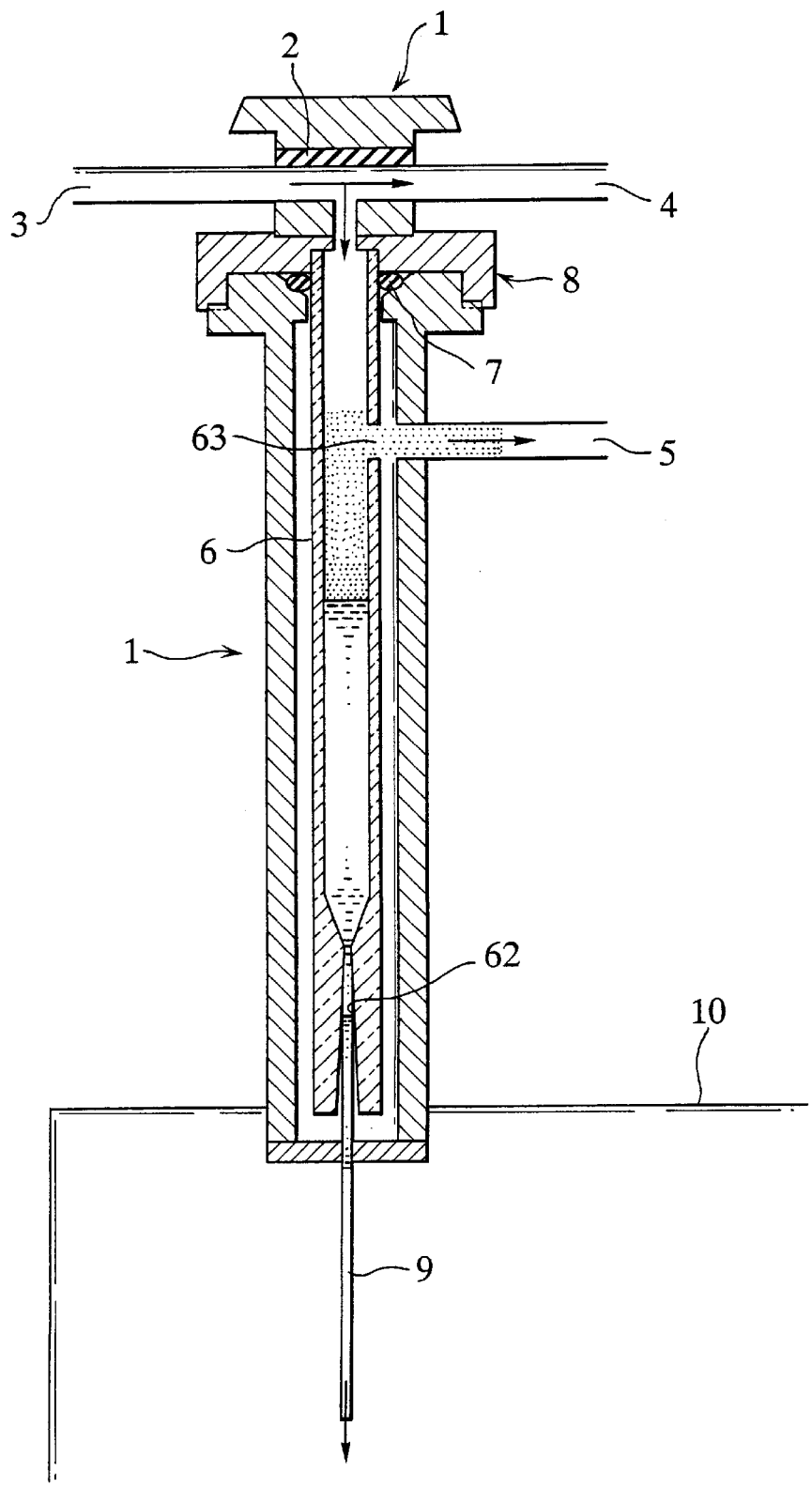
FIG. 1 is an explanatory sectional view of an embodiment of the present invention.

An embodiment of the present invention is explained hereunder.

Numeral 1 denotes the body of an injection port in the shape of a hollow cylinder. Injection port body 1 is made of glass or quartz and liner 6 is made of glass, quartz or metal for example steel, stainless steel. The top of the injection port body 1 is provided with a septum 2 and communicates with a carrier gas inlet 3 and a septum purge 4. Numeral 5 denotes a split purge, which is formed at the upper part of the injection port body 1. Numeral 6 represents a liner, which is inserted through the injection port body 1 and fastened therein with a cap nut 8. An O-ring 7 is disposed between the liner 6 and the cap nut 8. An opening 61 is formed at the top of the liner 6, while the bottom of the liner 6 is formed into a press-fit 62 so that a pre-column 9 may snugly be inserted thereinto. Although the pre-column 9 is used with a main column connected thereto under normal circumstances, it is possible to omit the pre-column 9 so that the main column alone may be inserted and fastened directly in the press-fit 62. Therefore, the term 'column' refers to a combination of a pre-column and a main column, or, in case no pre-column is used, the main column. The bottom of the injection port body 1 is immovably attached to an oven 10. The liner 6 is also provided with a discharge port 63, which is located at the upper part of the liner 6. Although the discharge port 63 may have any desired shape, examples of which include, but not limited to, a through hole, a slit and a gap, it is required to have such a shape as to enable the discharge of vapor resulting from evaporation of the solvent. Furthermore, it is advisable to form the discharge port 63 at a location where the solvent may vaporize and be discharged, desirably above the surface of the solvent and below the opening 61. Although it is convenient to form the split purge 5 and the discharge port 63 at the same height, it is not a requirement.

Figure 4:
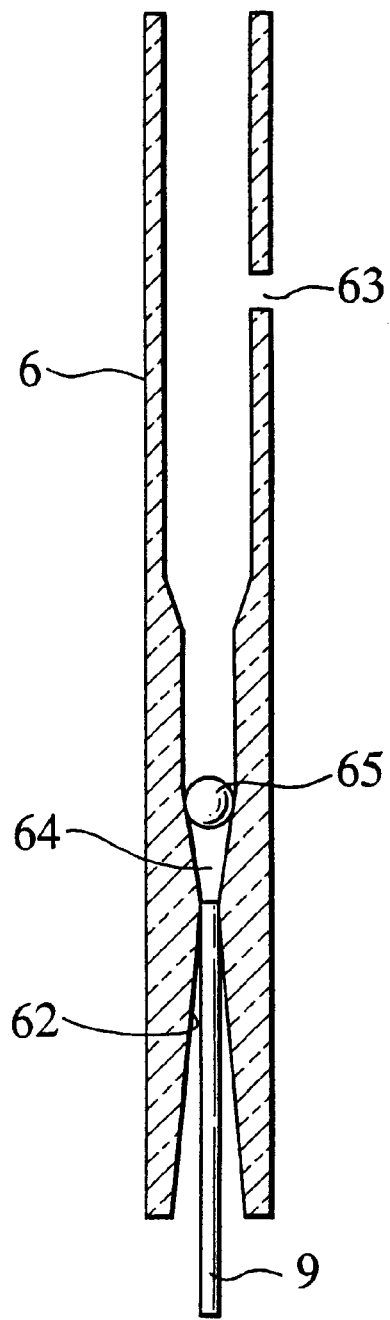
FIG. 4 is an explanatory sectional view of the principal part of yet another embodiment of the present invention.

Instead of specifically providing the liner 6 with a discharge port 63, the opening 61 at the upper end of the liner 6 may be used as a discharge port. In this case, a liner 6 having no special solvent discharge port is installed on a septum purge line 4, and elimination of the solvent is conducted by purging solvent vapor from the septum purge line 4. A tapered narrow portion 64 may be formed immediately above the press-fit 62 of the liner 6, and a resistance member 65 made of a glass bead or other appropriate material may be placed in the narrow portion 64. (See FIG. 4) In cases where a mass spectrometer is used as the detector, the carrier gas flows at a constant rate (0.5 ml/min.), because the entrance of the capillary column is in a vacuum. Should a sample be injected in this state, the sample in the state of a liquid tends to flow toward the column before the solvent is sufficiently heated. The above configuration shown in FIG. 4, wherein a glass bead is inserted to create resistance against the liquid sample, is capable of preventing the sample in the state of a liquid from flowing into the column. The above configuration has another benefit in that it provides resistance against the vertical vibration of the solvent after the solvent is injected.

It is recommended to provide an apparatus having any one of the configurations described above with a back-flush line 11 as shown in FIG. 5. To be more specific, the portion where the back-flush line 11 is connected to the pre-column 9 or the pre-column 9 and the main column is formed into a T-connection 111. The back-flush line 11 is formed by connecting a gas supply 112, which is adapted to feed the carrier gas or the like, to the T-connection 111 through a pressure regulator 113 comprised of a back pressure valve or the like, and a valve 114, which may be an electromagnetic valve. Although the T-connection 111 may be disposed in the oven 10, the back-flush line 11 has to be positioned outside the oven 10. The apparatus tends to become dirty when mass injection is conducted, and the above configuration, wherein the portion where the pre-column and the main column are connected is formed into a T-connection and connected to a back-flush line, is particularly effective in removing the contaminants. After the elimination of the solvent and the introduction of the desired constituent into the main column are completed, back-flushing is conducted to remove the contaminants.

EXAMPLE

Next, a detailed explanation is given of a method according to the invention, which uses an apparatus structured as described above.

A solvent and a sample are injected into the liner in a conventional manner. At that time, it is necessary that the temperature in the liner 6 be lower than the boiling point of the sample solvent and that the boiling point of the sample be higher than that of the solvent. The temperature of the interior of the oven 10 has to have been set higher than the boiling point of the solvent in order to prevent the solvent from flowing into the pre-column. For example, if acetone is used as the solvent in the state where the pressure of the carrier gas is 100 kPa, the solvent is in the state of a liquid with its vapor pressure being 72 kPa, when the temperature is 73° C. When the temperature is 78° C., the solvent is in the boiling state, i.e. a mixture of liquid and gas, with its vapor pressure being 100 kPa. At a temperature of 78° C., the solvent is in the gaseous state with its vapor pressure being 125 kPa. In other words, when the temperature in the injection port is maintained at 73° C., the acetone is in the state of a liquid and will not boil. However, the acetone evaporates so that its vapor pressure reaches 72 kPa. The acetone vapor exits from the discharge opening 63 and is discharged through the split purge 5 of the injection port body 1.

The acetone is discharged in a dispersed state with the vapor pressure of 72 kPa at 73° C. Therefore, given that split purge 5 has a discharge flow rate of 50 ml/min. and that the carrier gas is helium (He), the acetone is discharged at a rate of 10 ml/min. in the form of gas, even if He:acetone=8:2. When 100 μl of acetone completely vaporizes, it is calculated that its volume is increased to 33 ml. Therefore, it takes three minutes to complete the discharge. At a pressure of 100 kPa and a temperature of 78° C., the pressure reaches equilibrium between the liquid acetone and the part where the acetone is boiling. While this equilibrium is maintained, the acetone is discharged at a rate equivalent to the flow rate of the column, e.g. 1.5 ml/min. until the desired constituent, i.e. the component that is desired to be obtained, finally remains in the pre-column and becomes concentrated. Then, thermal desorption of the concentrated desired constituent is conducted by increasing the temperature of the oven 10.

The state described above is explained in detail, referring to FIGS. 2A–2D.

Because of the pressure equilibrium, the injected sample, which is still in the form of a liquid, remains in the liner and becomes concentrated, while the solvent alone vaporizes.

Figures 2A, 2B, 2C, 2D:
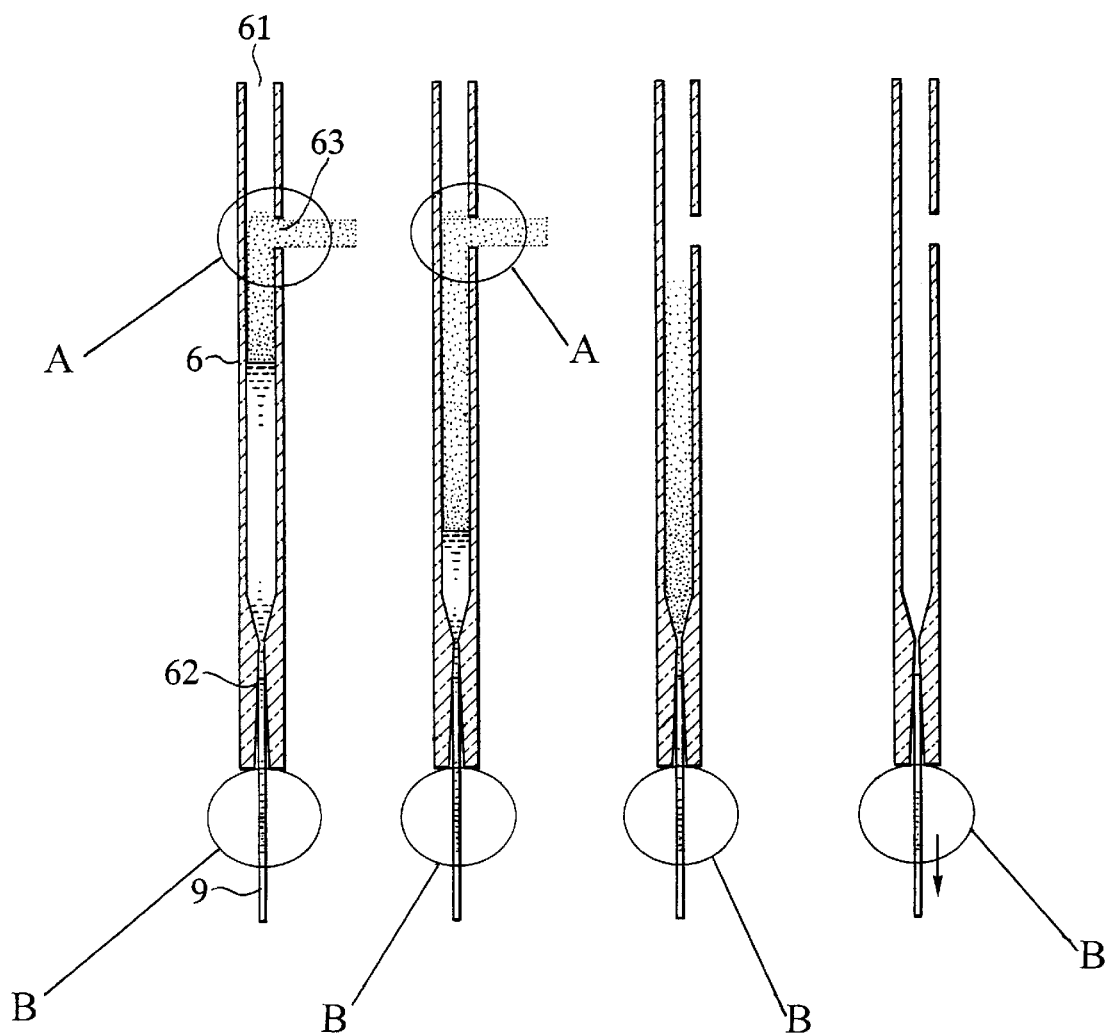
FIGS. 2A–2D are schematic illustrations of the principal part of same to explain how said embodiment operates.
Figure 3:
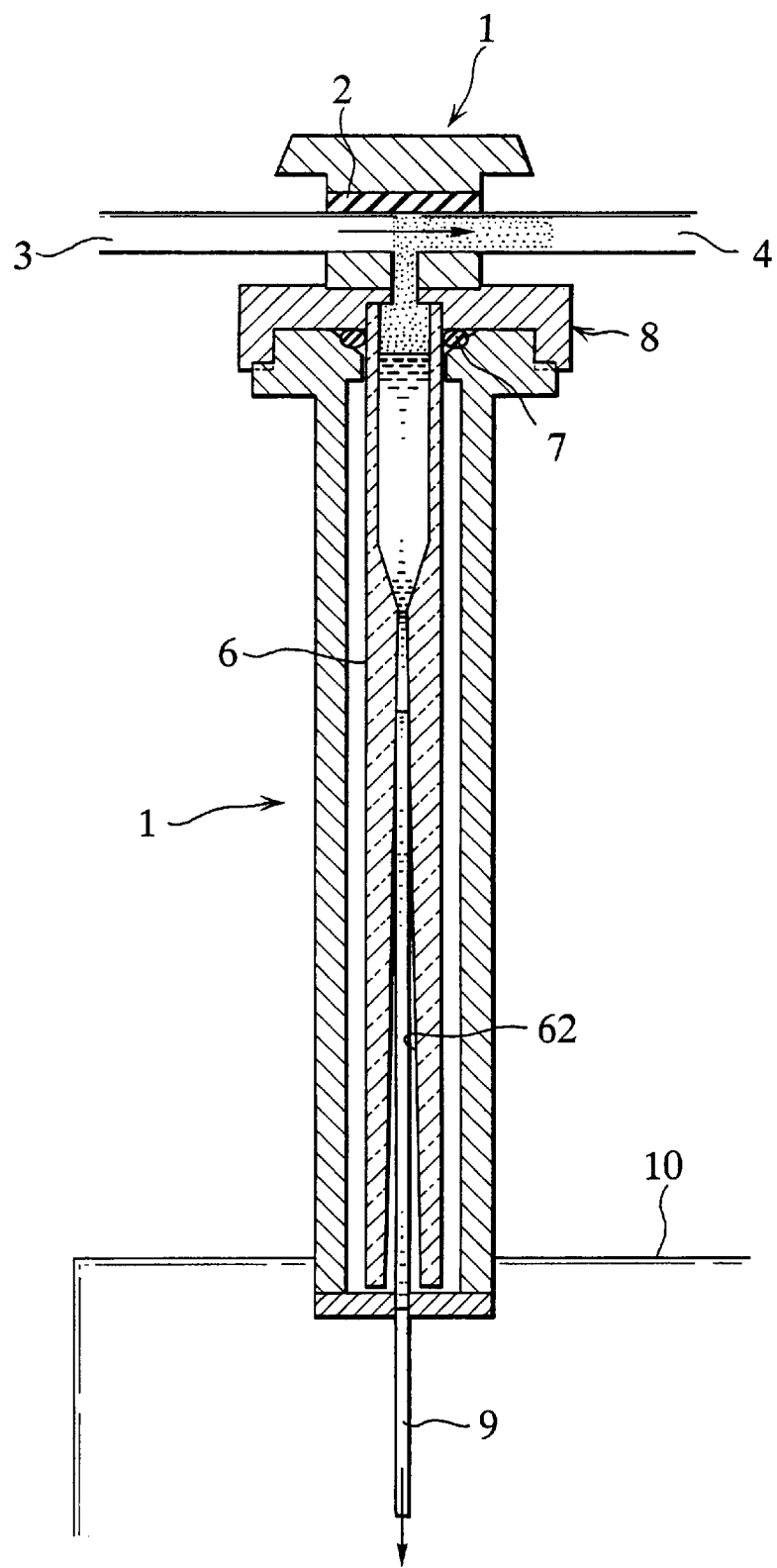
FIG. 3 is an explanatory sectional view of another embodiment of the present invention.

When the solvent is on the point of flowing toward the column, where the oven is installed, the solvent is pushed back by the vapor pressure, because the temperature of the oven is higher than the boiling point of the solvent. Should the solvent be pushed back too further, it is then pushed toward the oven, because the pressure of the carrier gas exceeds the pressure of the solvent vapor due to the low temperature in the injection port. Thus, the liquid (the sample) is retained at a point in the column, i.e. a location where its temperature is such that the pressure of the carrier gas is balanced with the pressure of the solvent vapor. The removal of the solvent is underway also at each portion enclosed with a circle and identified by the letter B. Turning to FIGS. 2A and 2B, although the solvent does not boil in the injection port, there is constant evaporation of the solvent. The solvent vapor resulting from the evaporation is removed through the split purge. The removal of the solvent at this portion, each of which portion is enclosed with a circle and identified by the letter A in these figures, is roughly several times more efficient than the removal of the solvent at the location B. As indicated in FIG. 2D, the desired constituent accumulated and concentrated here undergoes thermal desorption by increasing the temperature of the oven.

Figure 6:
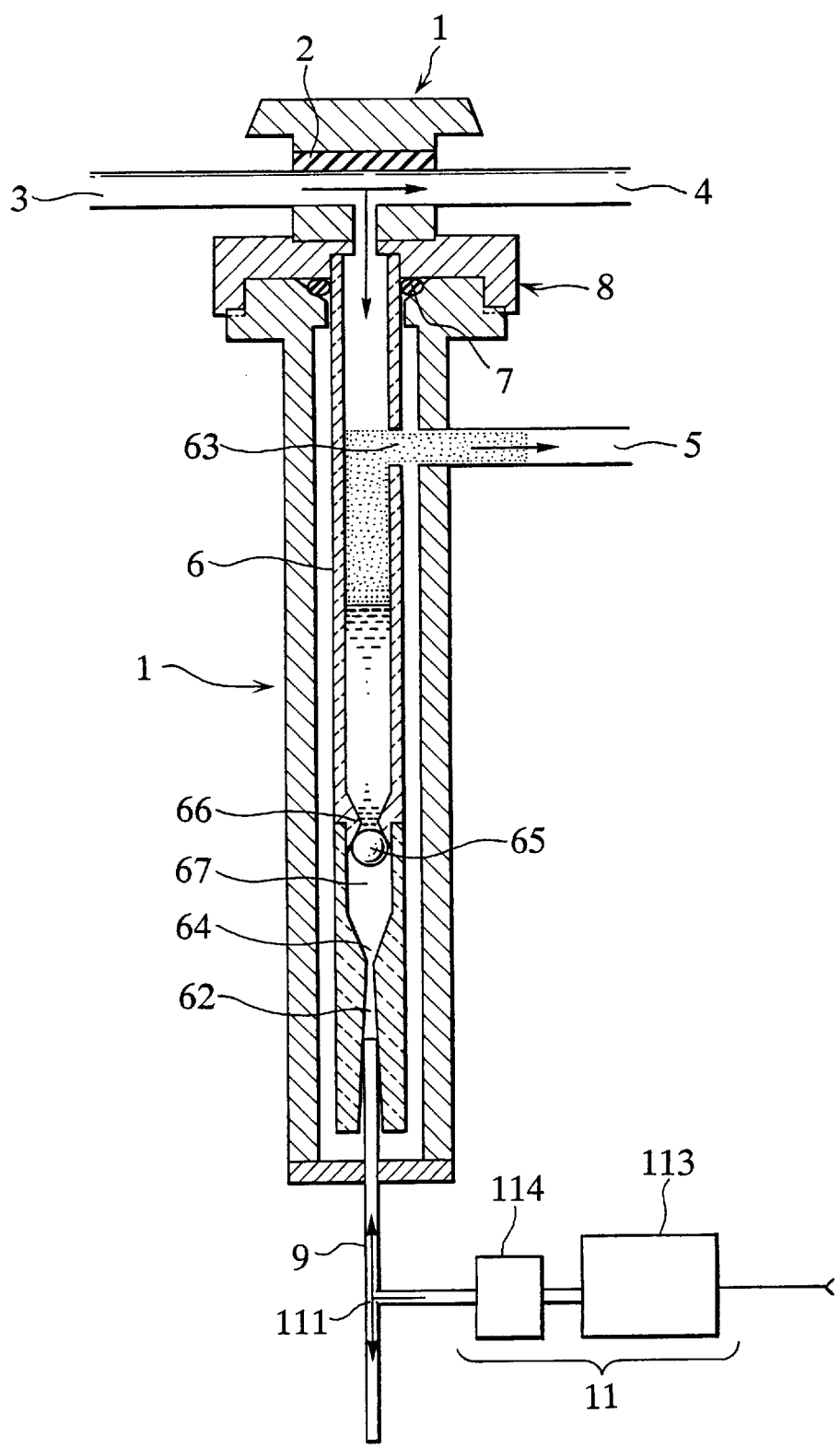
FIG. 6 is an explanatory sectional view of yet another embodiment of the present invention.

Next, another embodiment shown in FIG. 6 is explained hereunder.

Although the temperature of the oven has to be higher than the boiling point of the solvent according to the embodiments described above, using a back-flush line 11 enables the elimination of the solvent even when the temperature of the oven is not higher than the boiling point of the solvent.

The liner 6 includes a middle chamber 67, which is defined by a narrow portion 64 formed above the press-fit 62 and a second narrow portion 66 tapered upward and located at an appropriate distance from the narrow portion 64. A resistance member 65 made of a glass bead or other appropriate material is placed in the middle chamber 67. It is recommended to form the second narrow portion 66 in two or more parts so as to enable the positioning of the resistance member. The second narrow portion 66 may then be formed by insertion or screwing.

Figure 5:
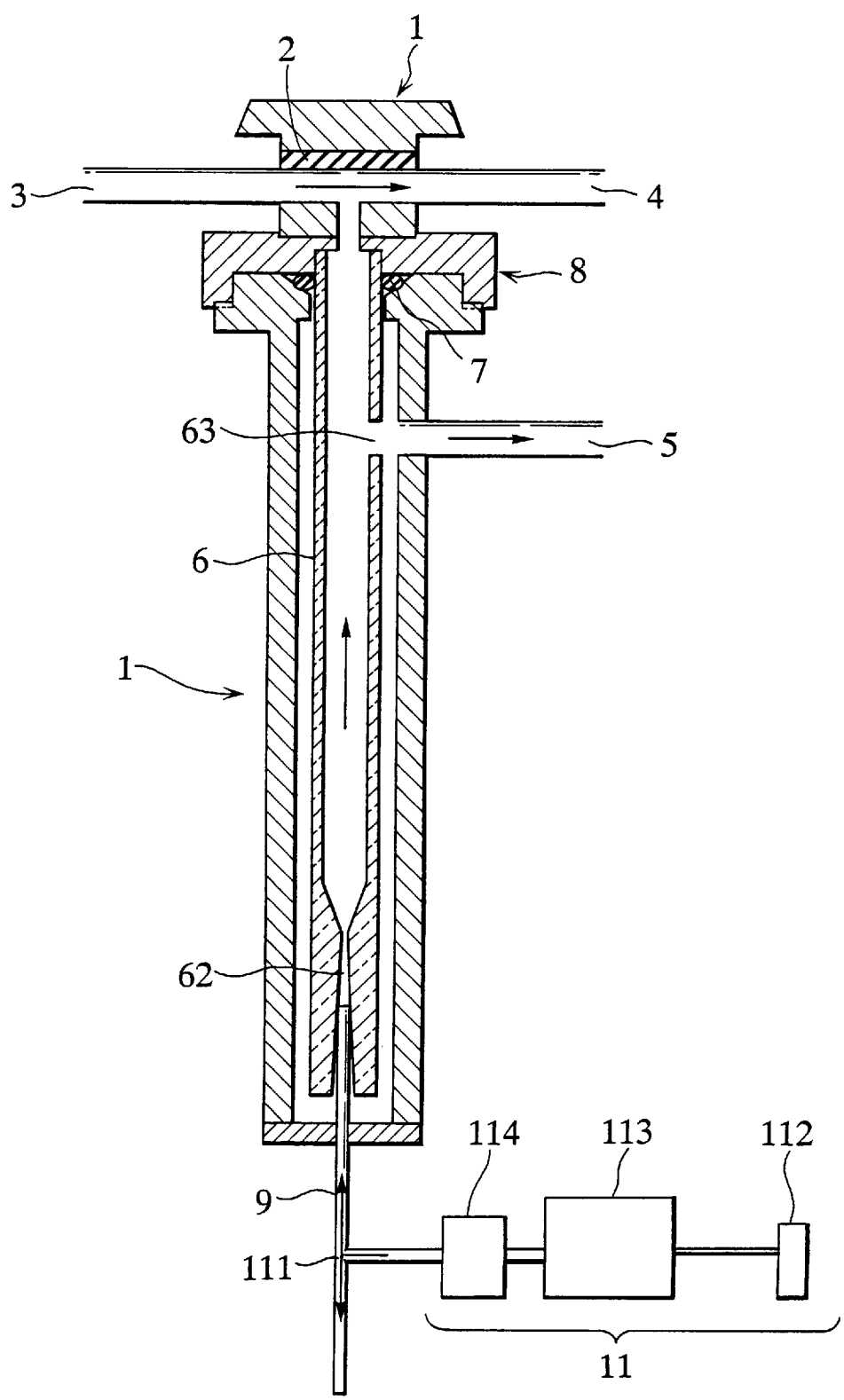
FIG. 5 is an explanatory sectional view of yet another embodiment of the present invention.

The back-flush line 11 shown in FIG. 6 may have the same structure as that shown in FIG. 5. According to the present embodiment, the pressure of back-flush causes the resistance member 65 to move into the second narrow portion 66 and close the same, thereby blocking off the middle chamber 67 and the portion located underneath the middle chamber 67 so that the sample can be retained therein.

When the apparatus described above is used, it is not always necessary to control the temperature of the oven, and the solvent is prevented from flowing into the oven by a physical means, i.e. action of the resistance member 65. Therefore, the temperature of the oven may be set low.

Figure 16:
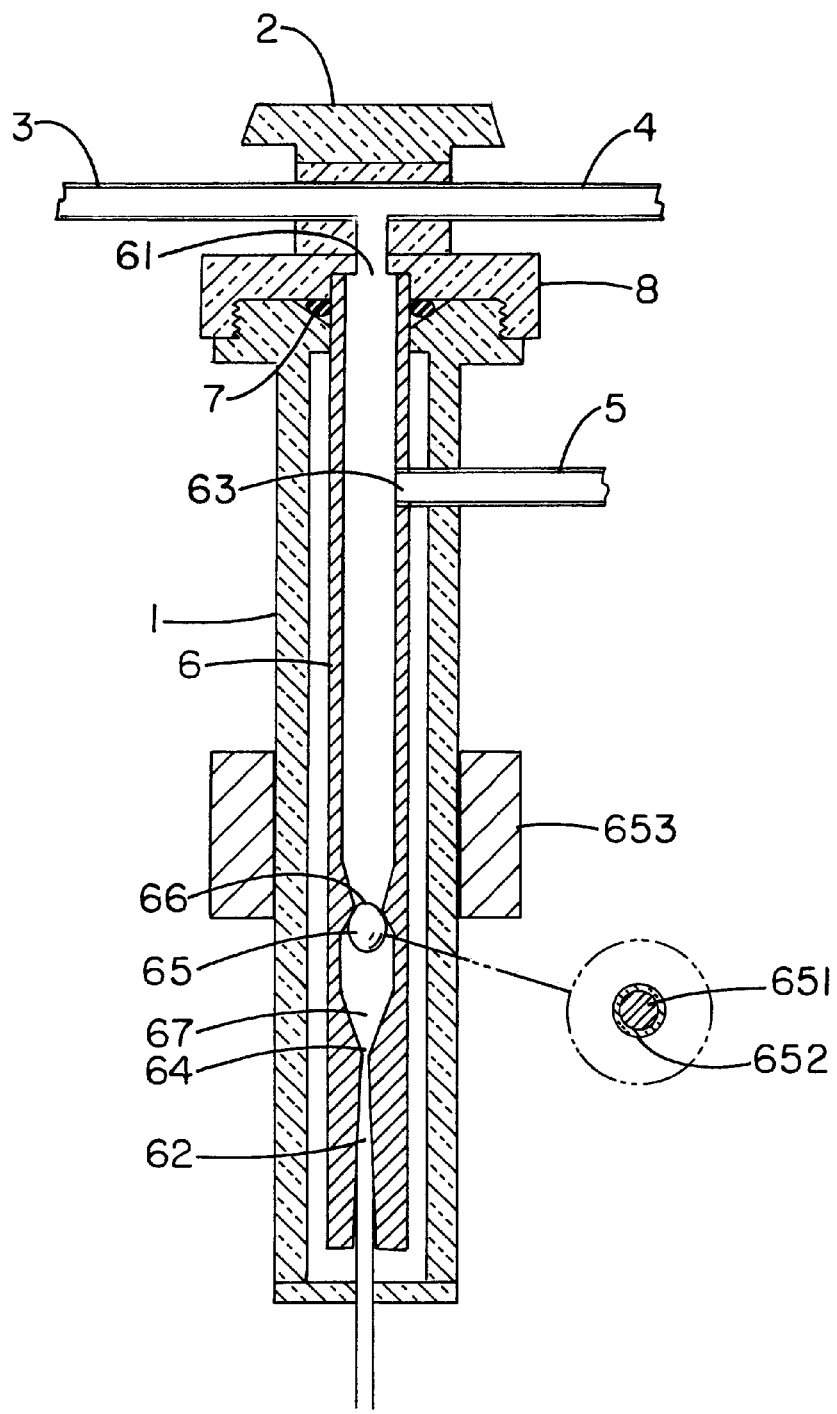
FIG. 16 is an explanatory sectional view of yet another embodiment of the present invention.

Referring to FIG. 16, the resistance member 65 is comprised of a core 651, which is formed of iron or other metal, and a coated layer 652 formed by coating the surface of the core 651 with an inert material, such as glass or quartz or ceramic precursor polysilazane.

Numeral 653 denotes a magnet, which may be an electromagnet. The magnet 653 is disposed outside the injection port body 1, at a location corresponding to the resistance member 65. The magnet 653 is either immovably positioned or is capable of moving up and down so that the resistance member 65 can be used for opening or closing the second narrow portion 66 and the press-fit 62; in other words, the second narrow portion 66 and the press-fit 62 can be opened or closed by using vertical movement or turning on and off of the magnet 653 of the resistance member 65.

Sample can be retained in liner 6 and the solvent is underway. Therefore, it is not always necessary to install a back-flush line 11 to open or close the second narrow portion 66.

Examples of G.C. Criteria

Pre-column: inactive silica capillary tube (a product of G.L. Science) having a length of 0.5 m×0.53 mm inside diameter Main column: NB-5 (a product of G. L. Science) having a length of 30 m×0.40 mm inside diameter Oven temperature: 82° C. (5 min.)→(20° C./min.)→300° C. (6 min.)

Temperature in injection port: 73° C. (5 min.)→(30° C./min.)→250° C. (6 min.)

Pressure in injection port: 100 kPa (5 min.)→160 kPa (6 min.)

Method of injection: split method (1:50 ml) 100 µl

The G.C. criteria for the present experiment have to be set so as to condense the desired constituent by evaporating only the solvent while maintaining the position of the solvent in the 0.53 mm ID pre-column as much as possible. Therefore, the program of the injection temperature, the pressure in the injection port and the temperature of the oven is explained hereunder, wherein the process to conduct evaporation of the solvent and concentration of the desired constituent is referred to as the first stage, and the separation measurement process is referred to as the second stage.

Injection Temperature Program

In the first stage, the temperature in the injection port is set lower than the boiling point of the solvent which corresponds to the current pressure in the injection port and the current temperature of the oven in order to prevent the solvent from boiling and enable it to remain in the liner in the form of a liquid when the solvent is injected into the liner. However, if the temperature in the injection port is set too low, it takes an exceedingly long period of time for the temperature in the injection port to decrease to the set temperature when the subsequent analysis is conducted. In the second stage, the temperature in the injection port is set higher than the temperature of the oven.

Program of Pressure in Injection Port

The pressure in the injection port in the first stage is set slightly higher than the pressure of the solvent vapor in order to prevent the solvent from boiling. In the second stage, the pressure is set so that the column flow rate is approximately 1 ml/min. in accordance with the temperature of the oven and that the linear velocity is in the range from 25 to 50 cm/sec.

Oven Temperature Program

In the first stage, the temperature of the oven is set higher than the boiling point of the solvent at the current pressure in the injection port in order to permit the solvent alone to evaporate while maintaining the position of the solvent in the 0.53 mm ID pre-column as steadily as possible by using the pressure. In the second stage, the temperature of the oven is increased in accordance with the column and the desired constituent.

Next, results of test conducted on various solvents are as follows:

Acetone

Criteria for Measurement Using GC/MS and Optic2-300

Apparatus for PTV Injection: Optic2-300

Gas chromatograph: HP5890 II FID

Pre-column: inactivated capillary column 0.53 mm I.d× 0.5 m

Main column: NB-5 0.25 mm I.d×30 m, 0.4 µm

Carrier gas: He, 40 kPa (3 min.)–8 kPa/min.–200 kPa

Oven temperature: 70° C. (3.5 min.)–15° C./min.–300° C. (4 min.)

Injection temperature: 65° C. (3 min.)–60° C./min.–280° C. (4 min.)

Injection mode: Split 30 ml/min.

Figure 7:
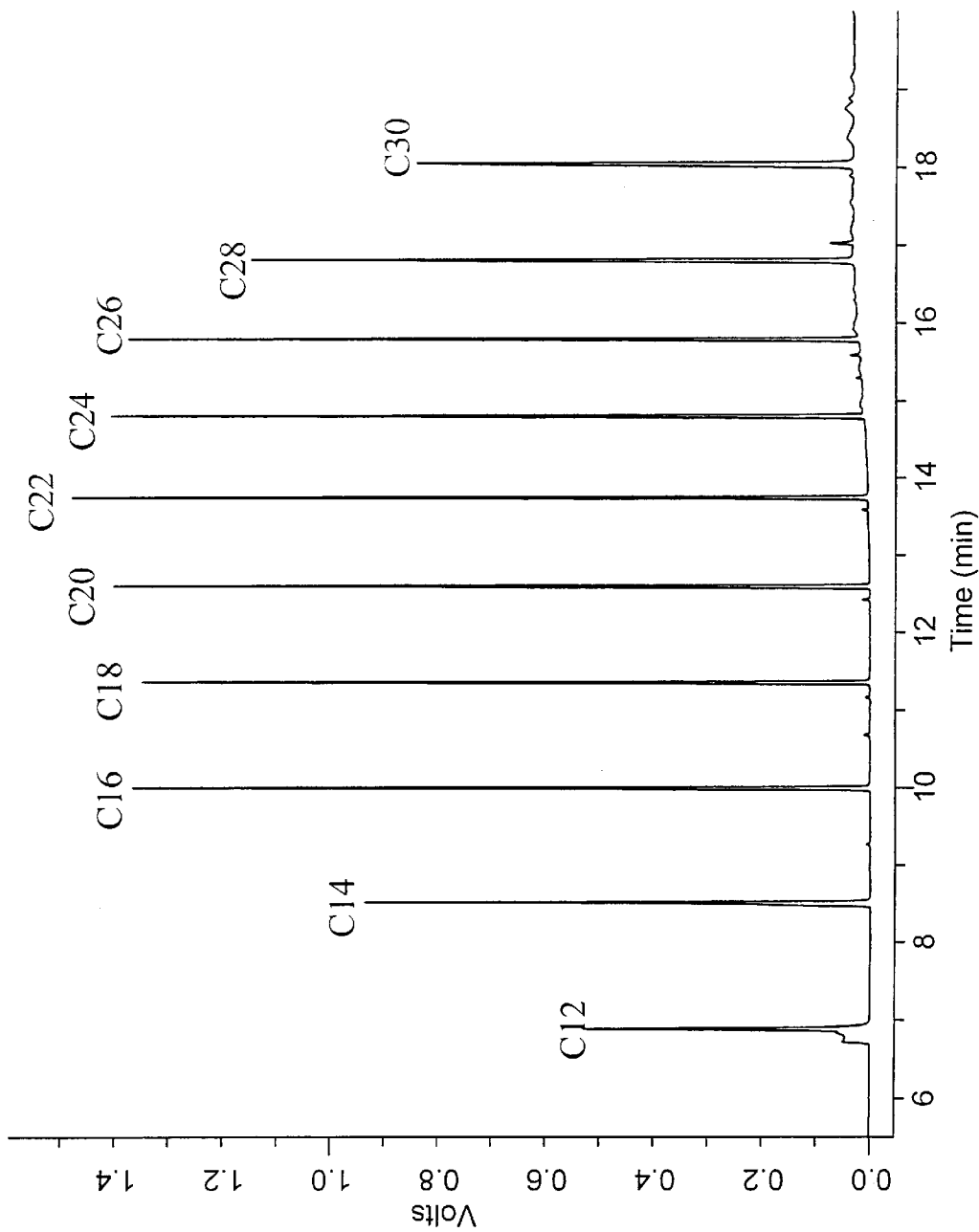
FIG. 7 is an analytical chromatogram using acetone.

Based on the above criteria, a test was conducted, using 1 ng/µl (1 ppm) of straight chain hydrocarbon C10–30 (even numbers only) as the sample. The results of the test are shown in FIG. 7.

Dichloromethane

Criteria for Measurement Using GC/MS and Optic2-300

Apparatus for PTV Injection: Optic2-300

Gas chromatograph: HP5890 II FID

Pre-column: inactivated capillary column 0.53 mm I.d× 0.5 m

Main column: NB-5 0.25 mm I.d×30 m, 0.4 µm

Carrier gas: He, 40 kPa (3 min.)–8 kPa/min.–200 kPa

Oven temperature: 54° C. (3.5 min.)–15° C./min.–300° C. (4 min.)

Injection temperature: 48° C. (3 min.)–60° C./min.–280° C. (4 min.)

Injection mode: Split 30 ml/min.

Figure 8:
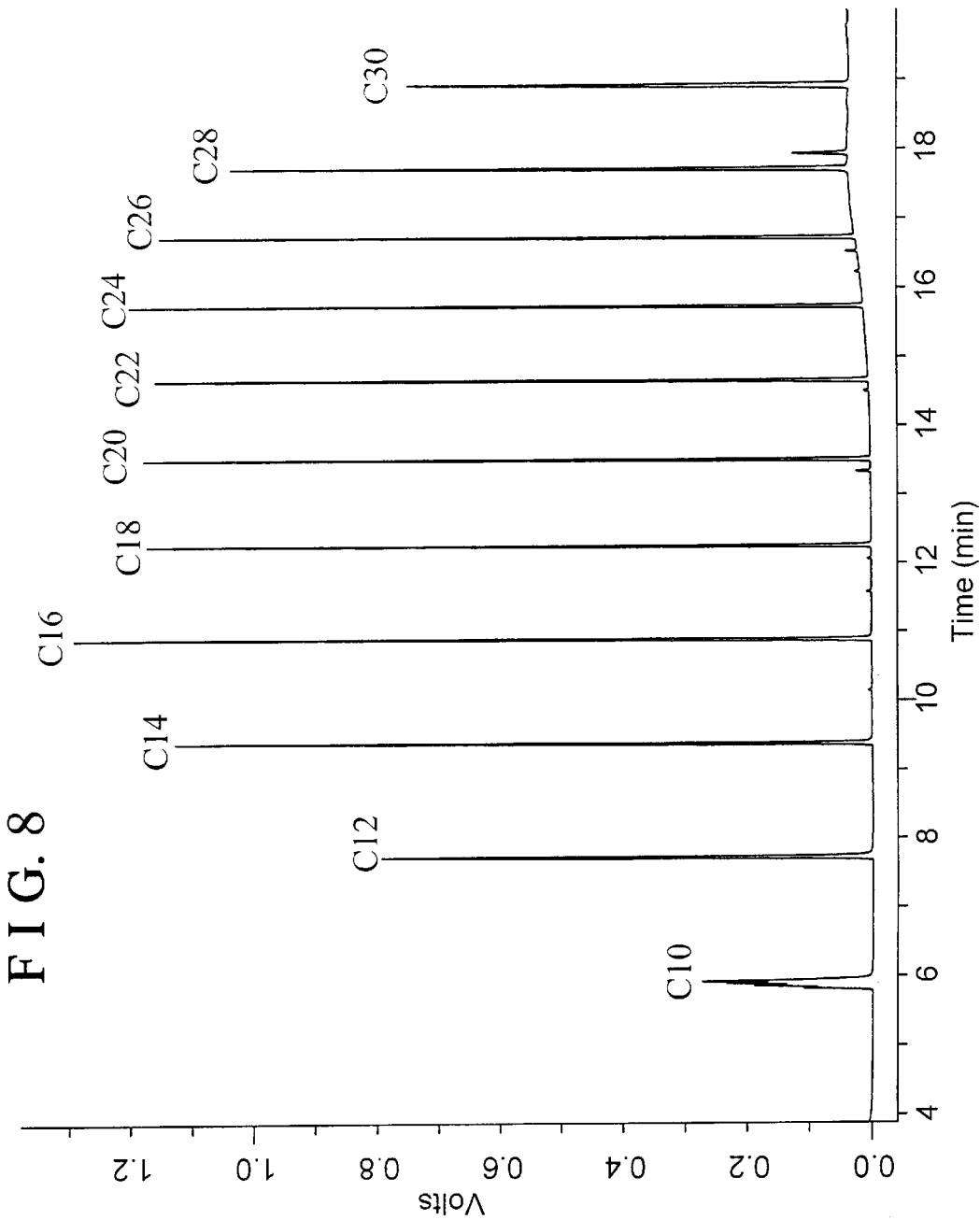
FIG. 8 is an analytical chromatogram using dichloromethane as the solvent.

Based on the above criteria, a test was conducted, using 1 ng/µl (1 ppm) of straight chain hydrocarbon C10–30 (even numbers only) as the sample. The results of the test are shown in FIG. 8.

Ethyl acetate

Criteria for Measurement Using GC/MS and Optic2-300

Apparatus for PTV Injection: Optic2-300

Gas chromatograph: HP5890 II FID

Pre-column: inactivated capillary column 0.53 mm I.d× 0.5 m

Main column: NB-5 0.25 mm I.d×30 m, 0.4 µm

Carrier gas: He, 40 kPa (3 min.)–8 kPa/min.–200 kPa

Oven temperature: 92° C. (3.5 min.)–15° C./min.–300° C. (4 min.)

Injection temperature: 86° C. (3 min.)–60° C./min.–280° C. (4 min.)

Injection mode: Split 30 ml/min.

Figure 9:
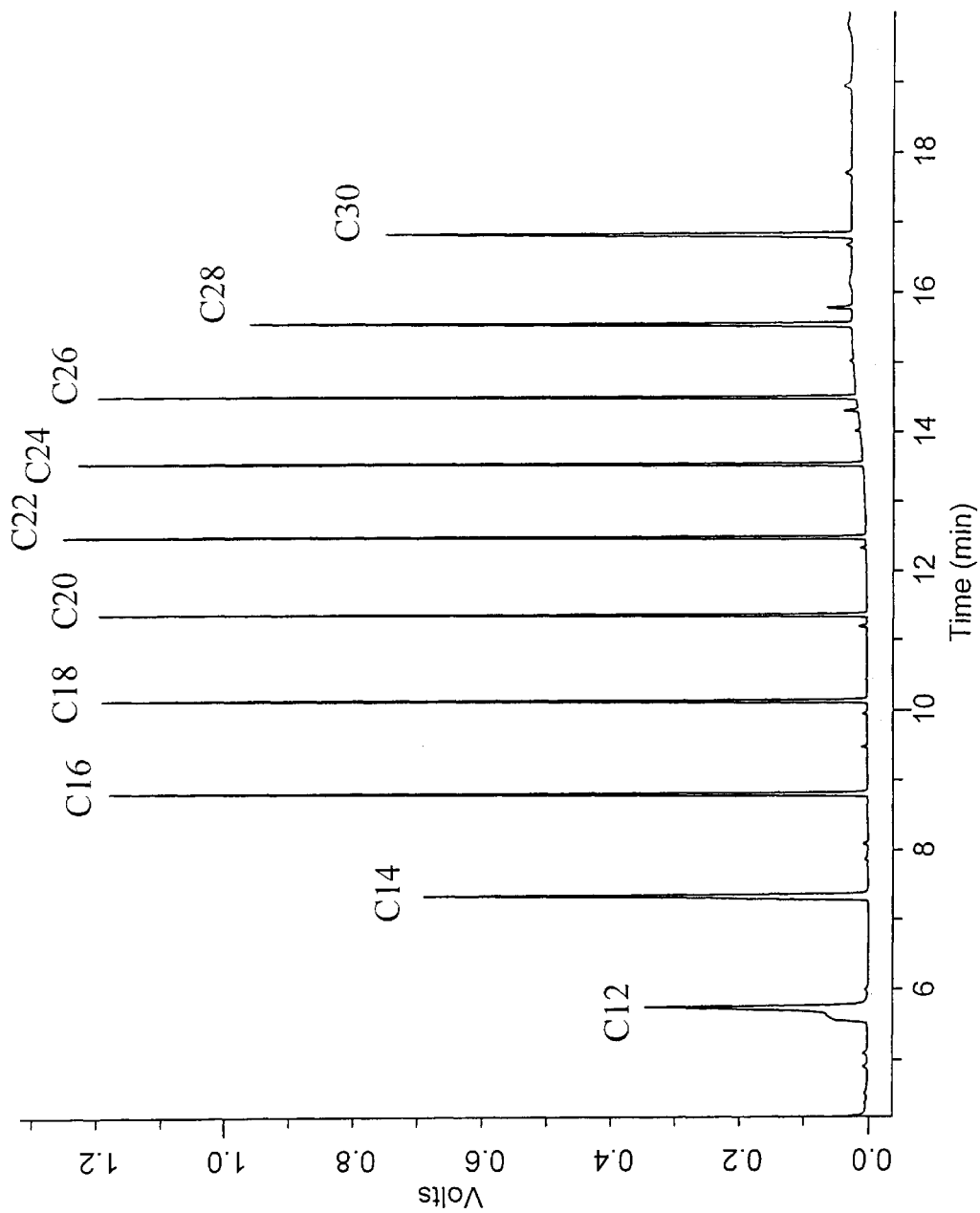
FIG. 9 is an analytical chromatogram using an acetic acid as the solvent.

Based on the above criteria, a test was conducted, using 1 ng/µl (1 ppm) of straight chain hydrocarbon C10–30 (even numbers only) as the sample. The results of the test are shown in FIG. 9.

Test 1 according to the invention

Criteria for Measurement Using GC/MS and Optic2-300

Apparatus for PTV Injection: Optic2-300

Gas chromatograph: HP5890 II FID

Main Spectrometer: HP5791

Pre-column: inactivated capillary column 0.53 mm I.d× 0.5 m

Main column: NB-5 0.25 mm I.d×30 m, 0.4 µm

Carrier gas: He, 40 kPa (3 min.)–8 kPa/min.–200 kPa

Oven temperature: 80° C. (4 min.)–20° C./min.–230° C. (1 min.)–30° C./min.–300° C. (6 min.)

Injection temperature: 72° C. (3 min.)–60° C./min.–280° C. (4 min.)

Injection mode: Split 30 ml/min.

Surface temperature: 300° C.

Method: SIM

Sample: standard sample (pollutants in the air in the room) 100 µl

Solvent: acetone

Figure 10:
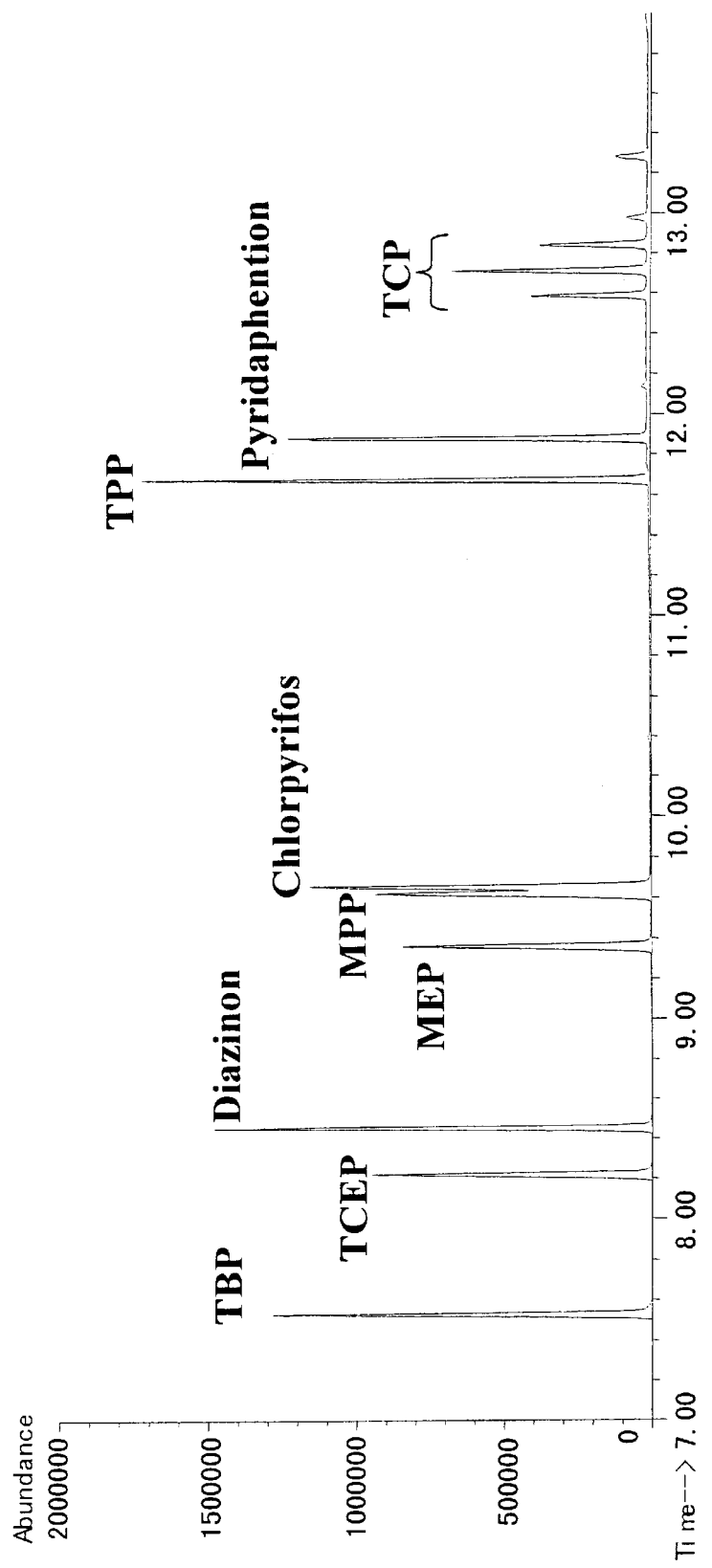
FIG. 10 is a chromatogram obtained by analysis according to an embodiment of the invention.

A test on the embodiment resulted in extremely precise analysis, which is shown in FIG. 10.

Test 2 according to the invention

Criteria for Measurement Using GC/MS and Optic2-300

Apparatus for PTV Injection: Optic2-300

Gas chromatograph: HP5890 II FID

Main Spectrometer: HP5791

Pre-column: inactivated capillary column 0.53 mm I.d× 0.5 m

Main column: NB-5 0.25 mm I.d×30 m, 0.2 µm

Carrier gas: He, 30 kPa (3 min.)–60 kPa (0.5 min.)–7 kPa

Oven temperature: 70° C. (3.5 min.)–15° C./min.–200° C. (3 min.)–5° C./min.–235° C.–15° C./min.–280° C. (3 min.)

Injection temperature: 62° C. (3 min.)–60° C./min.–280° C. (4 min.)

Injection mode: Split 30 ml/min.

Surface temperature: 300° C.

Method: SCAN

Figure 11:
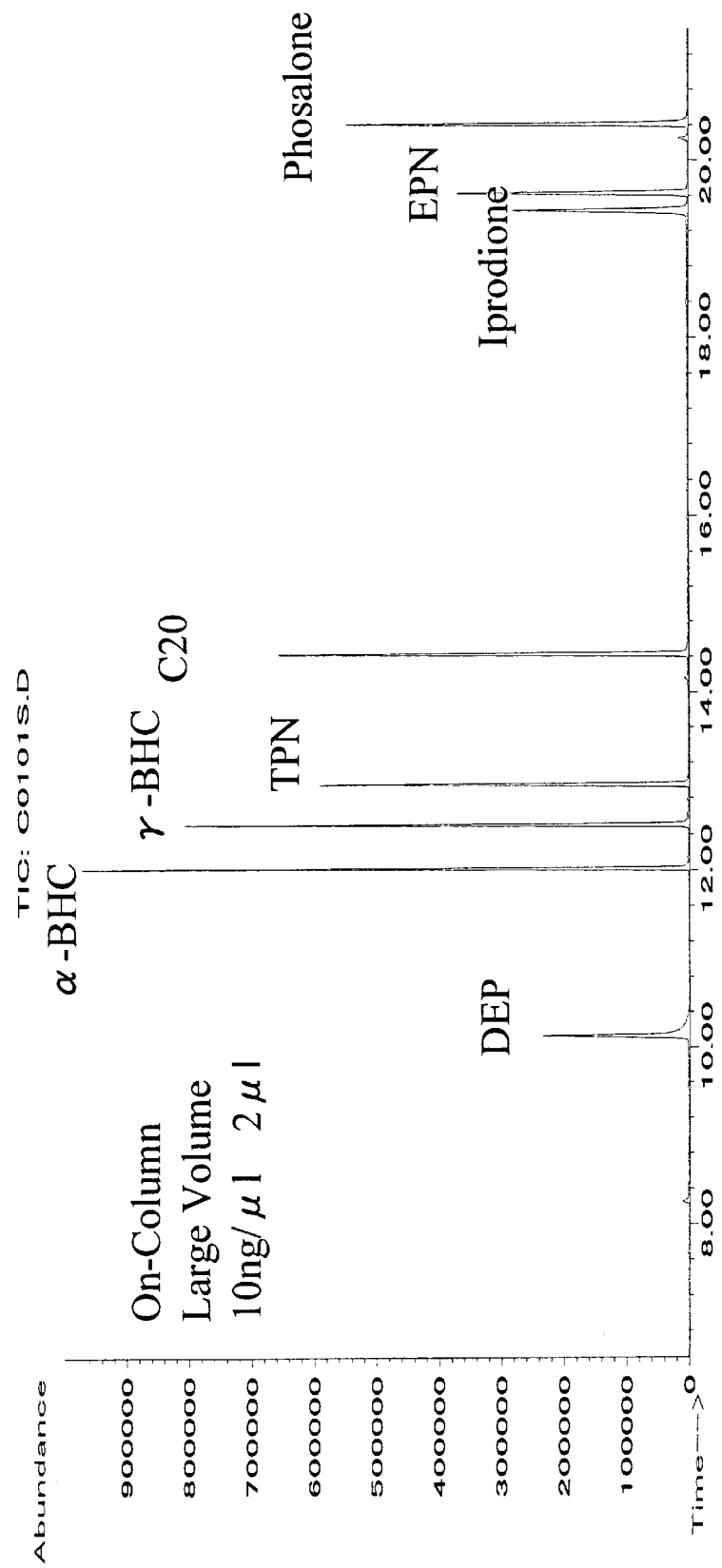
FIG. 11 is a chromatogram obtained by analysis according to another embodiment of the invention.

Sample: standard sample (agricultural pesticide prone to thermal decomposition) 100 µl Solvent: acetone Test results verify that the above embodiment enables the precise analysis even on a substance which would be decomposed by heat in cases where the analysis is conducted according to a method using a filler. Test results are shown in FIG. 11.

Next, tests were conducted on identical samples in accordance with different injection methods, i.e. an on-column method, a solvent discharge PTV method using a filler, and a method according to the invention.

Test

Samples were produced by adding $C_{20}$ serving as an internal standard to each chemical selected from the group consisting of DEP, α-BHC, β-BHC, TPN, iprodione, EPN and phosalone, all of which are agricultural chemicals that are easy to decompose during analysis, and diluting each mixture with acetone. By using a PTV injection port (Optic 2-300) as the injection port for each test, 2 µl, 100 µl and 100 µl of each sample was analyzed according to the on-column method, the PTV mass injection method using a filler, and the method according to the invention respectively, and a comparative evaluation was conducted regarding decomposition characteristics resulting from these methods. 48 g of Tenax TA 60-80 mesh was used as the PTV filler.

Test Results and Evaluation

Figure 12:
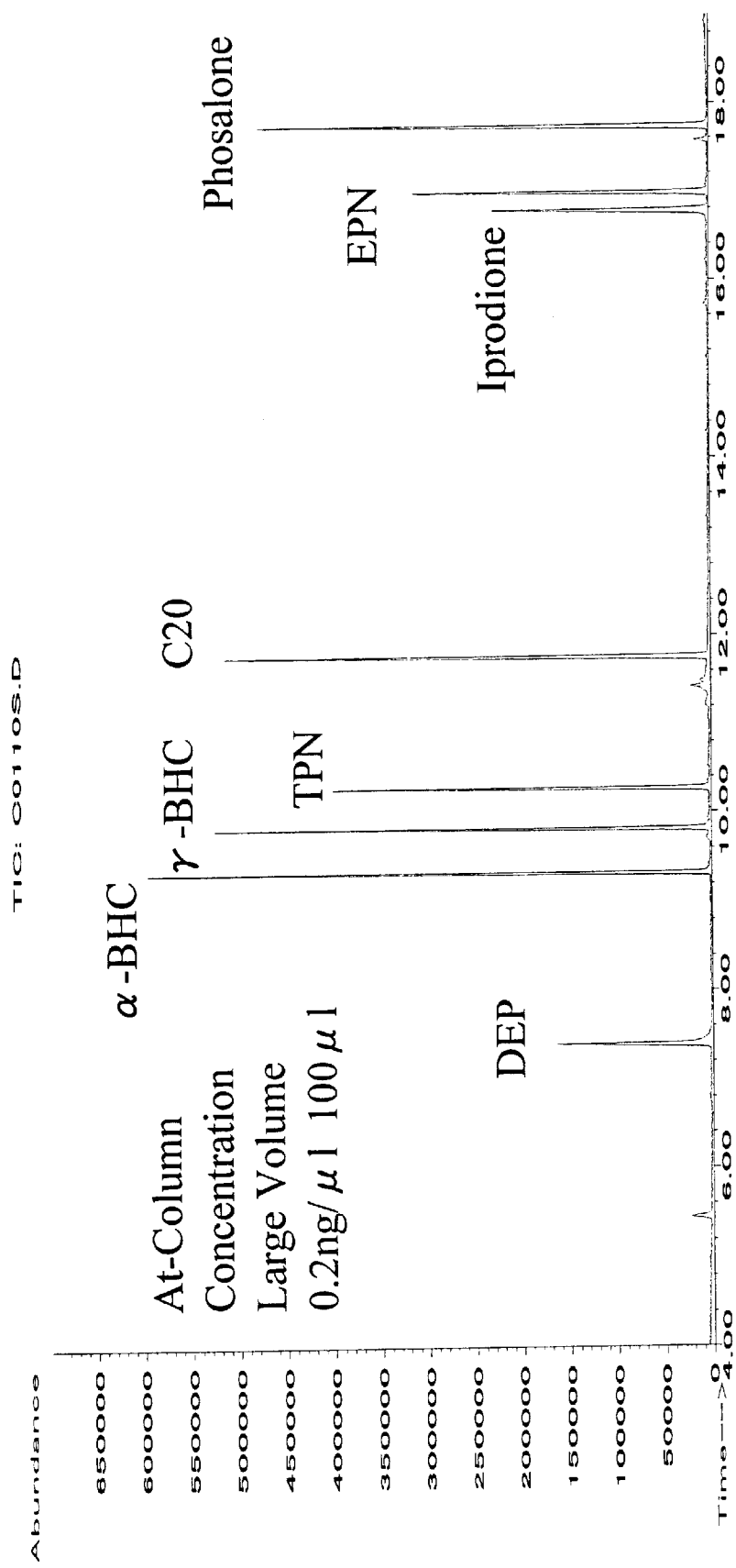
FIG. 12 is a chromatogram obtained by analysis according to an on-column method.
Figure 13:
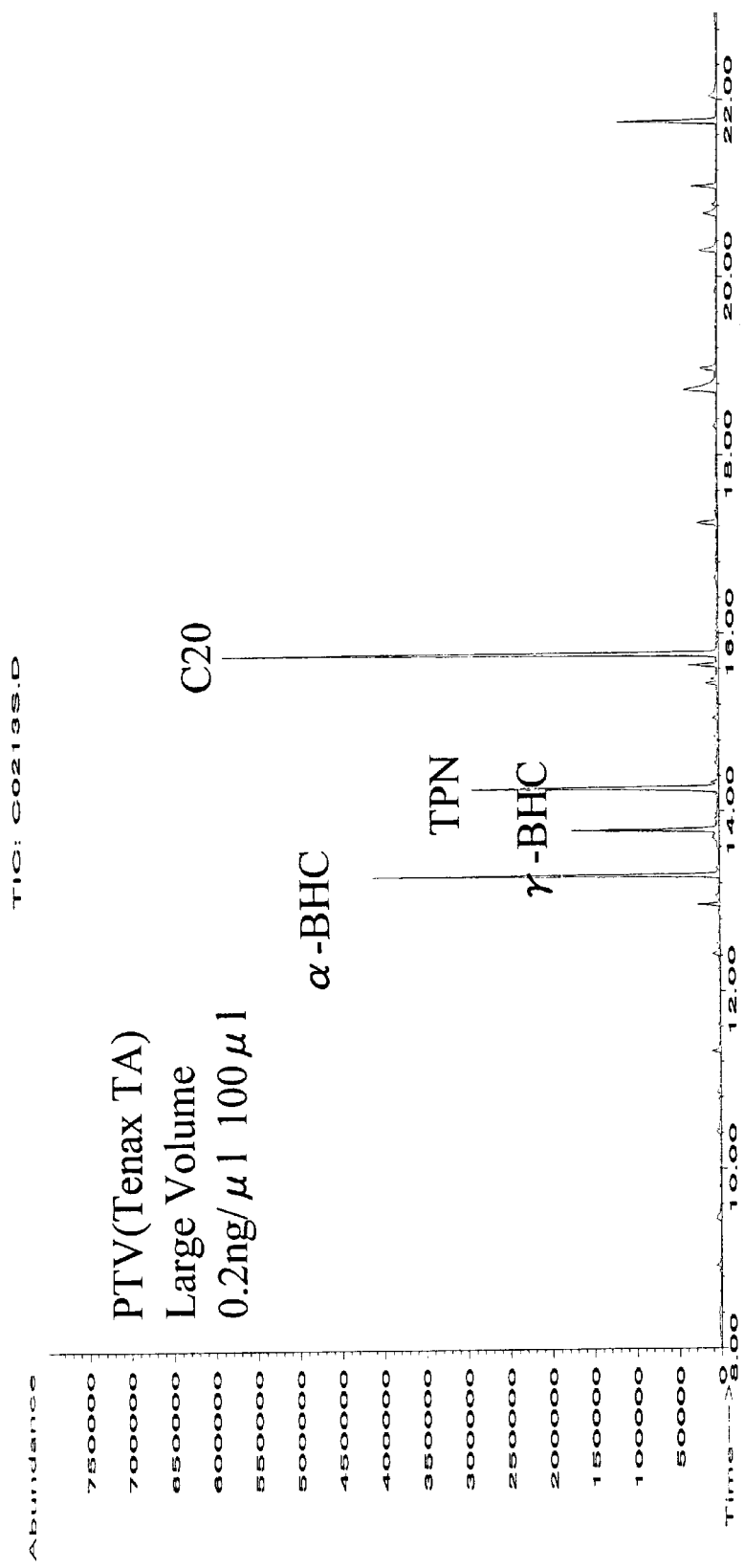
FIG. 13 is a chromatogram obtained by analysis according to a PTV mass injection method.
Figure 14:
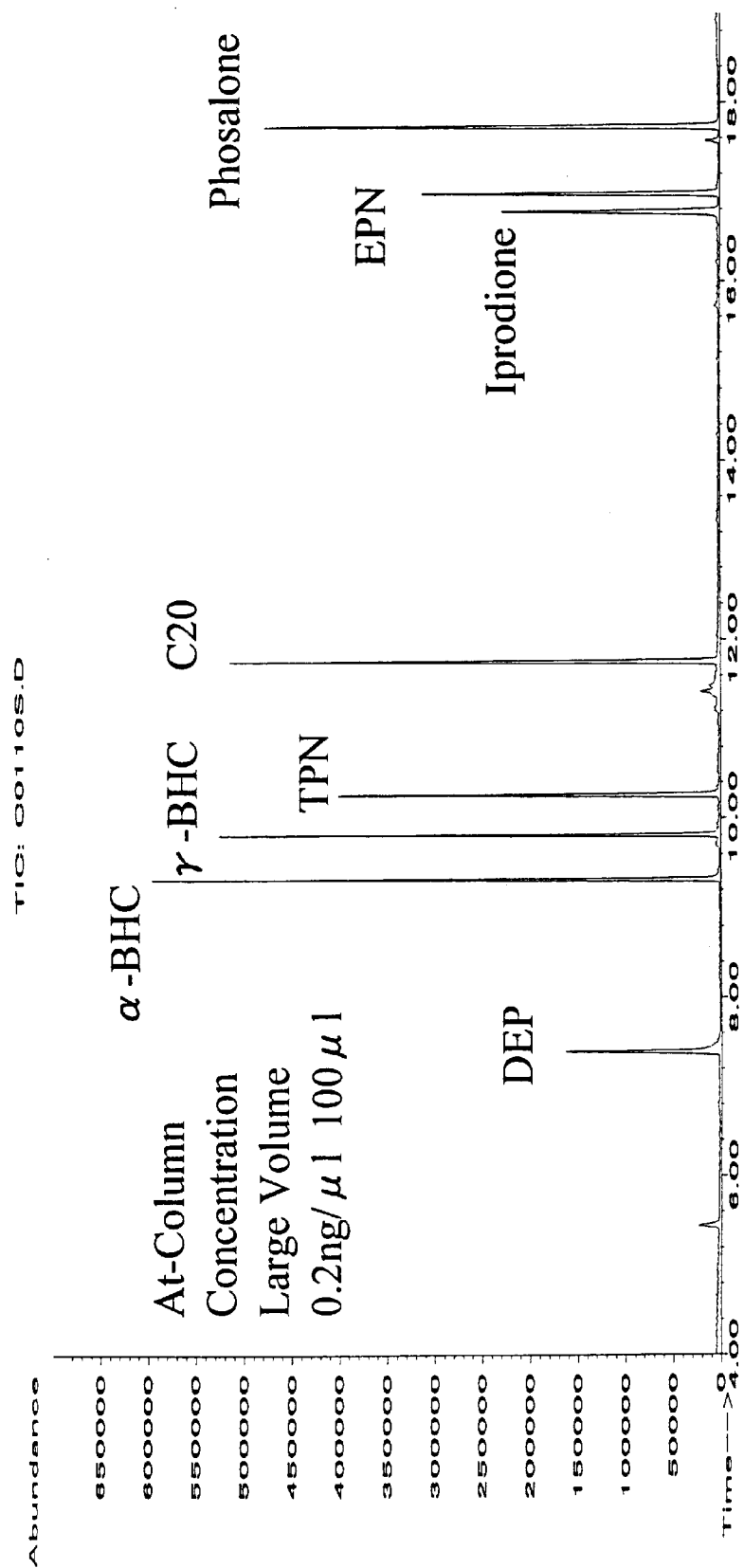
FIG. 14 is a chromatogram obtained by analysis according to a method of the present invention.

The chromatograms obtained by the methods specified above are respectively shown in FIGS. 12, 13 and 14.

Figure 15:
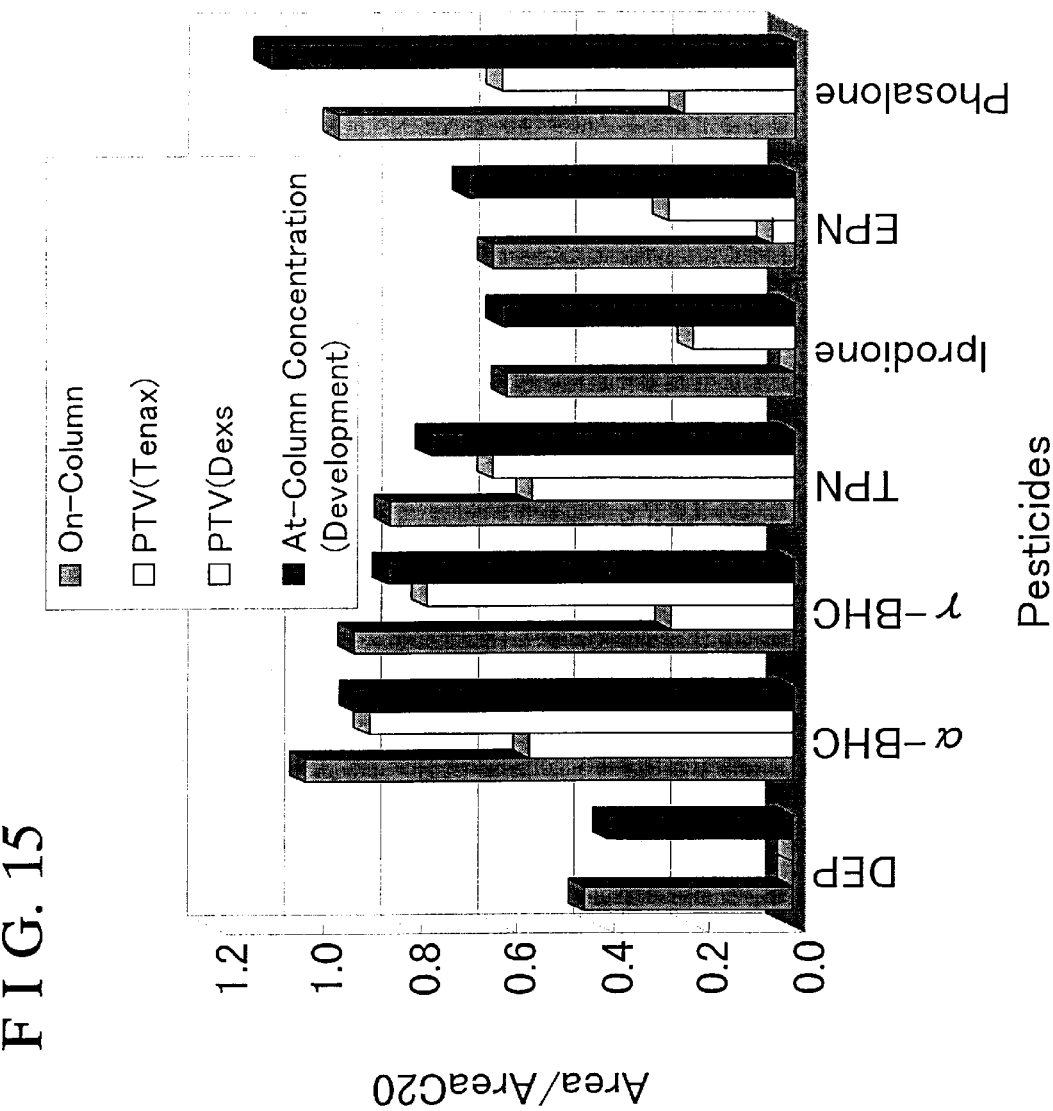
FIG. 15 is a comparison diagram of characteristics of decomposition of the agricultural chemicals resulting from said injection methods.

The on-column injection method shown in FIG. 12 calls for introducing a sample directly into a capillary column. As the temperature in the injection port is set low, no decomposition occurs in the injection port. On the other hand, mass injection is not possible, because the quantity of the sample that can be injected according to this method is limited to only 1 to 2 µl. As it is evident from comparison with $C_{20}$, the tests by the conventional PTV mass injection method shown in FIG. 13 resulted in complete decomposition of DEP, EPN and iprodione, and semi-decomposition of α-BHC, β-BHC and TPN. As shown in FIG. 14, the tests conducted by the injection method according to the invention not only produced results similar to those in FIG. 12, i.e. the analysis obtained through the on-column method or the like, but also enabled the injection of a large quantity of sample, i.e. 100 µl. Comparison of characteristics of decomposition of the agricultural chemicals resulting from said injection methods is shown in FIG. 15.

These results show that the PTV mass injection method using a filler brings about decomposition of samples. However, results of the tests conducted by the injection method according to the present invention were similar to those obtained through the on-column method and caused virtually no decomposition. This is probably because the injection method according to the invention is the same as the on-column method in principle, except for the process of elimination of the solvent. Therefore, the injection method according to the invention has proved to be suitable for mass injection sensitive analysis of agricultural chemicals, which are easy to decompose during analysis.

As described above, on aspect of the invention calls for providing the injection port with a liner, connecting the column and the liner to a press-fit, evaporating the solvent introduced into the liner, and discharging the evaporated solvent from a discharge port formed at the upper part of the liner. As the evaporated solvent is thus discharged quickly from the discharge port of the liner, the solvent can be removed in a short period of time, even if a great quantity of solvent is injected. Therefore, the invention is capable of coping with high speed injection and mass injection of samples.

Another aspect of the invention is also directed to providing the injection port with a liner, connecting the column and the liner to a press-fit, introducing a solvent and a sample into the liner and controlling the respective temperatures in the injection port and the oven so as to discharge the evaporated solvent from a discharge port formed at the upper part of the liner while accumulating and concentrating the desired constituent in the sample at the entrance of the column. As the method according to the invention is adapted to concentrate a sample without using a filler, it is free from the possibility of occurrence of residue or decomposition of the desired constituent. The invention also enables the reduction of the time required by elimination of the solvent by using a splitless liner which is capable of split-purging, or by discharging the solvent through a split purge. Furthermore, the invention is adapted to conduct at-column concentration at a point in the column, there is no need of a special, separate process of re-concentration. Furthermore, when a sample or other necessary substance is injected into the liner, there is virtually no influence of the injection rate. Yet another benefit of the method according to the invention lies in its efficiency: it permits injection to be conducted in several times and is easy to conduct mass injection and therefore free from the problems that are inevitable with the at-column method. In addition, it permits mass injection of samples.

Another aspect of the invention may limit the temperature in the injection port to no higher than the boiling point of the solvent and the temperature of the oven to no lower than the boiling point of the solvent, retaining the sample in the liner and the column causes the solvent in the sample to evaporate at a constant vapor pressure so that the solvent in the liner is removed through the split purge.

In the invention, the injection port may be provided with a liner; the column and the liner are connected to the press-fit; the body of the injection port is provided with a split; and a discharge port for discharging vapor of evaporated solvent is formed at the upper part of the liner. Therefore, there is no need of a liner having a special shape or dimensions, and a liner having normal dimensions is sufficient. In addition, the invention ensures steady positioning of the liner and easy insertion of a syringe, and provides an apparatus which is easy to produce and convenient to handle.

Also according to the invention, a resistance member 65 comprised of a glass bead or the like creates resistance against the liquid sample and is thus capable of preventing the sample in the state of a liquid from flowing into the column. The resistance member 65 also provides resistance against the vertical vibration of the solvent after the solvent is injected. Therefore, the invention as claimed in claim 4 or claim 8 is also applicable to cases where a mass spectrometer is used as the detector.

Also in the invention, contaminants accumulated in the pre-column, the liner, etc. due to mass injection of a sample or other substance can be removed by means of the back-flush line.

Also according to the invention, the pressure of back-flush causes the resistance member 65 to move into the second narrow portion 66 and close the same, so that the sample is retained therein. Therefore, it is not always necessary to control the temperature of the oven. As the solvent is prevented from flowing into the oven by the resistance member 65, the temperature of the oven is permitted to be set low.

What is claimed is:

1. A method for mass injection of a sample, said method comprising the steps of: providing an injection port with a liner; connecting a column to said liner; evaporating a solvent introduced into said liner; and discharging the evaporated solvent from a discharge port associated with said liner.

2. A method for mass injection of a sample, said method comprising the steps of: providing an injection port with a liner; connecting a column to said liner; introducing a solvent and a sample into said liner and controlling the temperatures in said injection port and an oven in which said column is disposed so as to discharge evaporated solvent from a discharge port associated with said liner while accumulating and concentrating at least one constituent in said sample at the column.

3. A method for mass injection of a sample as claimed in claim 2, wherein the temperature in the injection port is set lower than the boiling point of the solvent, and the temperature of the oven is set higher than the boiling point of the solvent.

4. A method of mass injection of a sample as claimed in claim 1 or claim 2, wherein an escape of a liquid sample is prevented by placing a resistance member in a narrow portion which is formed immediately above the connection of the column with the liner.

5. A method for mass injection of a sample as claimed in claim 1 or claim 2, wherein said column is provided with a back-flush line for feeding gas to the column, said back-flush line including a pressure regulator and a valve.

6. A method for mass injection of a sample as claimed in claim 5, wherein said liner includes a first narrow portion in said liner and a second narrow portion is formed above the first narrow portion, and a resistance member is placed between the second narrow portion and the first narrow portion so that the solvent is prevented by said resistance member from flowing into the second narrow portion and the portion of the liner located below the second narrow portion.

7. An apparatus for mass injection of a sample, wherein an injection port having a body is provided with a liner; a column connected to the liner; the body of the injection port is provided with a split purge; and a discharge port for discharging vapor of evaporated solvent is formed at an upper part of the liner.

8. An apparatus for mass injection of a sample as claimed in claim 7, wherein a narrow portion is formed in said liner above the connection with said column, and a resistance member is placed in said narrow portion.

9. An apparatus for mass injection of a sample as claimed in claim 7, wherein the column is provided with a back-flush which communicates with a gas supply source for feeding a carrier fluid and includes a pressure regulator and a valve.

10. An apparatus for mass injection of a sample as claimed in claim 7, wherein said liner comprises a first narrow portion and a second narrow portion formed above the first narrow portion, at a predetermined distance from the connection to said column, and a resistance member is placed between said first and second narrow portions.

11. An apparatus for mass injection of a sample as claimed in claim 10, wherein:

the resistance member is formed of a metal coated with an inert material, and;

a magnet is disposed outside the body of the injection port so that said resistance member can be controlled.

* * * * *